(12) United States Patent  
Guo et al.

(10) Patent No.: US 11,589,976 B2  
(45) Date of Patent: Feb. 28, 2023

(54) MULTI-LUMEN STENT GRAFT

(71) Applicant: HANGZHOU ENDONOM MEDTECH CO. LTD., Zhejiang (CN)

(72) Inventors: Wei Guo, Zhejiang (CN); Yongsheng Wang, Zhejiang (CN); Anwei Li, Zhejiang (CN); Liman Shang, Zhejiang (CN)

(73) Assignee: HANGZHOU ENDONOM MEDTECH CO. LTD., Hangzhou (CN)

( * ) Notice: Subject to any disclaimer, the term of this patent is extended or adjusted under 35 U.S.C. 154(b) by 31 days.

(21) Appl. No.: 16/765,016

(22) PCT Filed: Nov. 20, 2018

(86) PCT No.: PCT/CN2018/116543  
§ 371 (c)(1),  
(2) Date: May 18, 2020

(87) PCT Pub. No.: WO2019/101076  
PCT Pub. Date: May 31, 2019

(65) Prior Publication Data  
US 2020/0352699 A1 Nov. 12, 2020

(30) Foreign Application Priority Data  
Nov. 24, 2017 (CN) .......................... 201711192781.9

(51) Int. Cl.  
*A61F 2/07* (2013.01)  
*A61F 2/06* (2013.01)

(52) U.S. Cl.  
CPC .......... *A61F 2/07* (2013.01); *A61F 2002/061* (2013.01); *A61F 2210/0014* (2013.01); *A61F 2250/0098* (2013.01)

(58) Field of Classification Search  
CPC .................. A61F 2/07; A61F 2002/061; A61F 2002/072; A61F 2250/0098  
See application file for complete search history.

(56) References Cited

U.S. PATENT DOCUMENTS 6,585,756 B1 7/2003 Strecker  
2005/0010277 A1 1/2005 Chuter  
(Continued)

FOREIGN PATENT DOCUMENTS

CN 1870951 A 11/2006  
CN 102014791 A 4/2011  
(Continued)

OTHER PUBLICATIONS

International Search Report issued in International Application No. PCT/CN2018/116545, dated Jan. 30, 2019, pp. 1-2, State Intellectual Property Office of the P.R. China, Beijing, China.

(Continued)

*Primary Examiner* — Jennifer Dieterle  
*Assistant Examiner* — Rebecca Lynee Zimmerman  
(74) *Attorney, Agent, or Firm* — Hauptman Ham, LLP

(57) ABSTRACT

A multi-lumen stent graft including a tubular main body stent graft and a tubular connection stent graft; the main body stent graft includes a tubular main body stent; the main body stent includes a tubular main body covering and a main body support frame fixed on a wall of the main body covering; a main lumen and at least one sub lumen are separated axially by a separation covering within the main body stent; in a released state, a proximal end of the connection stent graft and the main lumen at a distal end of the tubular main body stent graft are fitted and connected together. The multi-lumen stent graft is not prone to (Continued)

endoleaks and displacement, which can simplify surgical operations, reduce the difficulty and risk of surgery, and has a wide range of applications.

20 Claims, 6 Drawing Sheets

(56) References Cited

U.S. PATENT DOCUMENTS

| | | | |
|---|---|---|---|
| 2006/0184228 | A1 | 8/2006 | Khoury |
| 2009/0177265 | A1 | 7/2009 | Dierking et al. |
| 2011/0270379 | A1 | 11/2011 | Bruszewski |
| 2014/0135905 | A1 | 5/2014 | Hung et al. |
| 2014/0277335 | A1 | 9/2014 | Greenberg et al. |
| 2015/0057737 | A1 | 2/2015 | Ondersma et al. |
| 2016/0081787 | A1* | 3/2016 | Parodi ............... A61F 2/07 623/1.14 |
| 2016/0278910 | A1 | 9/2016 | Kelly |
| 2017/0000630 | A1 | 1/2017 | Shames et al. |
| 2017/0156846 | A1* | 6/2017 | Wang ............... A61F 2/89 |
| 2017/0319359 | A1* | 11/2017 | Mehta ............... A61F 2/07 |
| 2018/0206972 | A1* | 7/2018 | Arbefeuille ......... A61F 2/848 |
| 2020/0214857 | A1* | 7/2020 | Youssef ............. A61F 2/852 |

FOREIGN PATENT DOCUMENTS

| | | |
|---|---|---|
| CN | 105213076 A | 1/2016 |
| CN | 105228561 A | 1/2016 |
| CN | 105662650 A | 6/2016 |
| CN | 106109056 A | 11/2016 |
| CN | 106456314 A | 2/2017 |
| CN | 205924245 U | 2/2017 |
| CN | 106687074 A | 5/2017 |
| WO | 2008021557 A1 | 2/2008 |
| WO | 2014172501 A2 | 10/2014 |
| WO | 2016154502 A1 | 9/2016 |

OTHER PUBLICATIONS

International Search Report issued in International Application No. PCT/CN2018/116543, dated Feb. 26, 2019, pp. 1-2, State Intellectual Property Office of the P.R. China, Beijing, China.

Chinese First Search Report issued in Chinese Application No. 201810899831.5, p. 1, State Intellectual Property Office of the P.R. China, Beijing, China.

Chinese Office Action issued in Chinese Application No. 201810899831. 5, pp. 1-5, State Intellectual Property Office of the P.R. China, Beijing, China.

The Supplementary European Search Report issued corresponding to EP Application No. EP18880850 dated Dec. 10, 2020.

The Supplementary European Search Report issued corresponding to EP Application No. EP18882101 dated Dec. 1, 2020.

The International Search Report issued corresponding to International Application No. PCT/CN2018116542 dated Jan. 23, 2019.

The International Search Report issued corresponding to International Application No. PCT/CN2018116544 dated Feb. 18, 2019.

The International Search Report issued corresponding to International Application No. PCT/CN2018116546 dated Feb. 18, 2019.

The second Office Action issued corresponding CN application No. 201810899831.5 dated Jul. 7, 2020.

\* cited by examiner

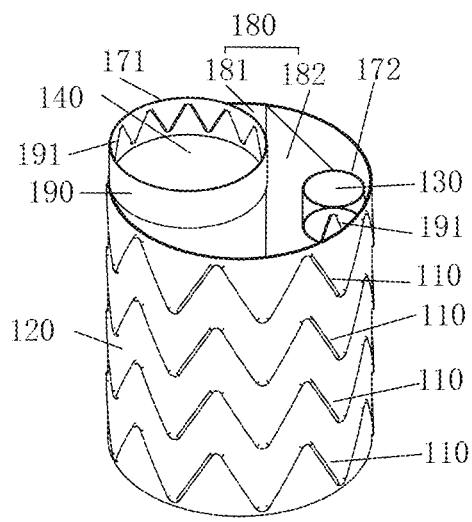
FIG. 14
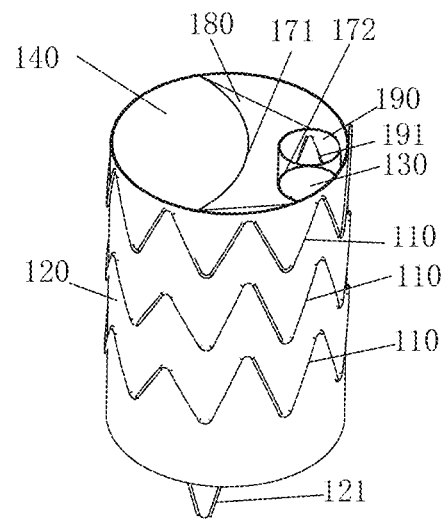
FIG. 15a
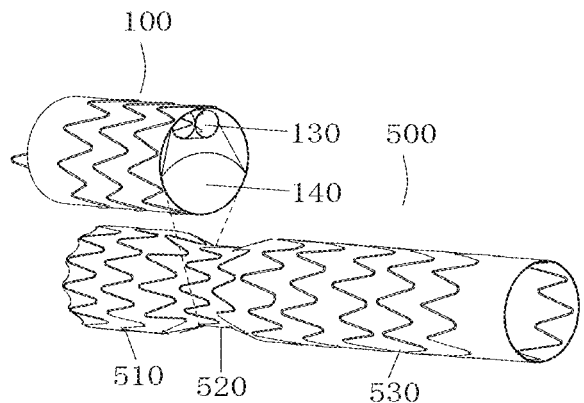
FIG. 15b
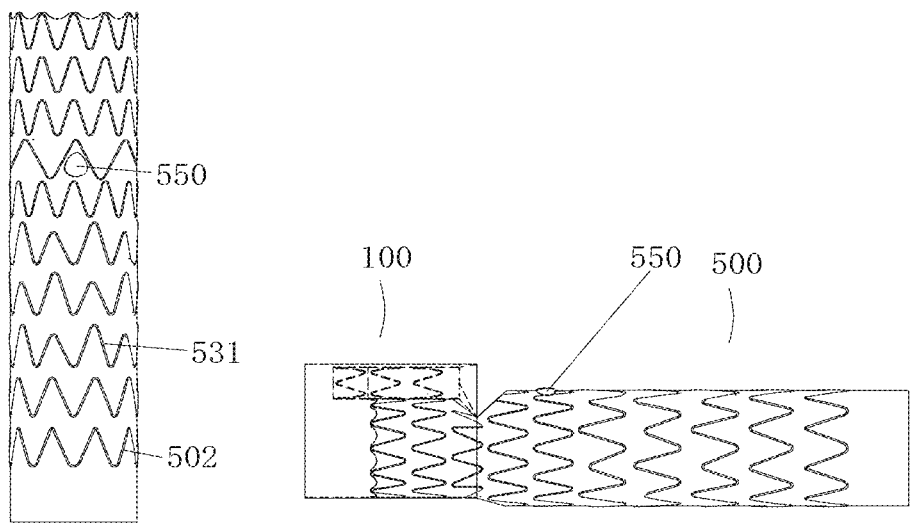
FIG. 16
FIG. 17

MULTI-LUMEN STENT GRAFT

CROSS REFERENCE TO RELATED APPLICATIONS

This application is the National Stage filing under 35 U.S.C. 371 of International Application No. PCT/CN2018/116543, filed on Nov. 20, 2018, which claims the priority and benefit of Chinese Application CN 201711192781.9, filed on Nov. 24, 2017. The contents of all afore-mentioned applications are hereby incorporated by reference in their entireties.

TECHNICAL FIELD

Aspects of the present disclosure relate to the technical field of medical equipment, particularly a stent graft. More specifically, certain implementations of the present disclosure relate to a multi-lumen stent graft used for interventional treatment of vascular diseases.

BACKGROUND

Aortic aneurysm refers to the local or diffusive abnormal expansion of the aortic wall, which causes symptoms due to compression of surrounding organs, and its main danger is tumor rupture. It usually occurs in the a, aortic arch, descending thoracic aorta, thoracoabdominal aorta, and abdominal aorta. Aortic aneurysms can be divided into true aortic aneurysms and pseudo aortic aneurysms by structure. The aortic aneurysm causes an increase in the inner pressure of the blood vessel, so it is progressively enlarged. If it develops for a long time, it eventually ruptures. Larger tumors are more likely to rupture. According to statistics, without surgery, 90% of thoracic aortic aneurysms patients die within 5 years, and 75% of abdominal aortic aneurysms patients die within 5 years.

Aortic dissection is another serious aortic disease. Aortic dissection refers to the destruction of the thoracic aorta medial membrane, bleeding in the vessel wall, and blood entering between the medial and adventitia of the vessel wall. Due to the impact of blood flow, once the aortic dissection is formed, the tear can be extended in the direction of blood flow, the dissection and the false lumen are enlarged, and the true lumen is compressed. Therefore, the dangers that may occur in patients with aortic dissection include: (1) the threat of complete rupture of the blood vessel, and once the blood vessel is completely ruptured, the mortality rate is extremely high; (2) the dissection is gradually enlarged, and the true lumen is compressed, so that the blood vessel supplied at the distal end is decreased. In most cases, aortic dissection is secondary to or coexisting with aortic aneurysm. The Oxford vascular disease study in the UK shows that the incidence of aortic dissection in natural populations is about 6/100,000 per year, with more men than women, with an average age of onset of 63 years.

Aortic diseases may involve branch arteries. Once branch arteries are involved, it will be difficult to solve them through interventional methods. At present, endovascular treatment of aortic disease has been carried out all over the world, that is, a minimally invasive method, which involves implanting a vascular stent into a lesioned artery through a vascular lumen to treat an arterial disease and improve blood supply, thereby achieving the purpose of treatment. The arterial blood vessel stent in the blood vessel lumen is composed of a tubular rigid wire stent and a polymer film fixed on the outside of the tubular rigid wire stent. The tubular rigid wire stent is made by folding elastic rigid wires in a Z shape to be enclosed into a ring, and then stitching or gluing multiple rings with a polymer film to form a stent graft. When used, the stent graft is compressed axially and loaded into a delivery device, and the delivery device passes the smaller femoral artery, the iliac artery, and the brachial artery to reach the lesioned artery, and then the stent graft is released. Due to the elastic force of the metal wire stent, it is automatically restored to a straight tube and is closely attached to the inner wall of the aorta.

In the prior art, commonly used stents involving arterial branch therapy include chimney stents, integrated multi-branch stents, and window-type stents. These stents are limited by the structure of the stents, often require temporary customization, or are prone to problems such as leakage. For example, the chimney stent has a "groove" between the small stent and the main body stent of the aorta, and there is a risk of leakage. On the other hand, the main body stent of the aorta is released in parallel with the small stent, and the main body stent may press the small stent, causing the blood flow at the small stent to be disturbed or even blocked.

SUMMARY

The technical problem to be solved by the present disclosure is to provide a multi-lumen stent graft with a structure that is not prone to endoleaks and displacement, which simplifies surgical operations, reduces the difficulty and risk of surgery, and has a wide range of adaptations.

The technical solutions adopted by the present disclosure to solve the technical problems are:

a multi-lumen stent graft, including a tubular main body stent graft and a tubular connection stent graft;

the main body stent graft includes a tubular main body stent; the main body stent includes a tubular main body covering and a main body support frame fixed on a wall of the main body covering; and a main lumen and at least one sub lumen are separated axially by a separation covering within the main body stent;

in a released state, a proximal end of the connection stent graft and the main lumen at a distal end of the tubular main body stent graft are fitted and connected together.

Further, with respect to the multi-lumen stent graft, preferably a distal end of the main lumen is provided with a main lumen opening, and an outer diameter of the proximal end of the connection stent graft is relatively larger than the main lumen opening of the main body stent graft; in the released state, the proximal end of the connection stent graft is fitted and connected with the main lumen by the main lumen opening.

Further, with respect to the multi-lumen stent graft, preferably the connection stent graft is a non-isodiametric stent or an isodiametric stent.

Further, with respect to the multi-lumen stent graft, preferably the connection stent graft is an isodiametric stent, and a side wall of the isodiametric stent is provided with a window in which a small branch is embedded; when the main body stent graft and the connection stent graft are fitted, the window in with the small branch is embedded is disposed close to the sub lumen of the main body stent graft.

Further, with respect to the multi-lumen stent graft, preferably the connection stent graft is a non-isodiametric stent composed of, from a proximal end to a distal end sequentially, a first tubular body, a second tubular body, and a third tubular body; a diameter of the second tubular body is smaller than a diameter of the first tubular body and a diameter of the third tubular body.

Further, with respect to the multi-lumen stent graft, preferably the connection stent graft is a non-isodiametric stent; a window in which a small branch is embedded is provided on the second tubular body of the non-isodiametric stent or a transition portion disposed between the second tubular body and the third tubular body; when the main body stent graft and the connection stent graft are fitted, the window in which the small branch is embedded is provided close to the sub lumen of the main body stent graft Further, with respect to the multi-lumen stent graft, preferably the connection stent graft is a non-isodiametric stent whose diameter of the proximal end is larger than the diameter of the distal end, and the diameter of the non-isodiametric stent is tapered from the proximal end to the distal end.

Further, with respect to the multi-lumen stent graft, preferably the connection stent graft includes a connection covering and a connection support frame fixed on the connection covering.

Further, with respect to the multi-lumen stent graft, preferably the connection support frame is a high-low wave stent or an equal-height wave stent, and the high-low wave stent is a partially-sutured stent.

Further, with respect to the multi-lumen stent graft, preferably a support rod is fixed axially along an outer wall of the connection covering.

Further, with respect to the multi-lumen stent graft, preferably the support rod is disposed on the connection covering on a side near the sub lumen.

Further, with respect to the multi-lumen stent graft, preferably, at least one fixing point is disposed between the support rod and the connection covering for fixing both together.

Further, with respect to the multi-lumen stent graft, preferably a transverse covering is provided at least between the distal end of the main body covering and the separation covering, and the main body covering and the separation covering are connected together by the transverse covering.

Further, with respect to the multi-lumen stent graft, preferably in an axial direction, the end faces of the main lumen opening, the sub lumen opening, and the main body covering are even at least at the distal end;

or the end face of at least one of the main lumen opening and the sub lumen opening is higher or lower than the end face of the main body covering.

Further, with respect to the multi-lumen stent graft, preferably at least one of the main lumen and the sub lumen includes a cylindrical extension covering extending from the transverse covering to the distal end;

an end face of the extension covering end face forms a main lumen opening, and the main lumen opening is below or flush with the end face of the main body covering;

or the end face of the extension covering forms a sub lumen opening, and the sub lumen opening is higher than, lower than, or flush with the end face of the main body covering.

Further, with respect to the multi-lumen stent graft, preferably an inner wall or an outer wall of the extension covering is provided with an extension support frame for supporting the extension covering.

Further, with respect to the multi-lumen stent graft, preferably the transverse covering is a planar structure perpendicular to a central axis of the main body stent;

or the transverse covering is an inclined surface structure not perpendicular to the central axis of the main body stent;

or the transverse covering includes at least one planar structure and at least one inclined surface structure, and the planar structure and the inclined surface structure are integral or are connected together.

Further, with respect to the multi-lumen stent graft, preferably the main lumen opening and the sub lumen opening are respectively provided with radiopaque markers for displaying positions of each opening of the shunt during surgery.

Further, with respect to the multi-lumen stent graft, preferably the radiopaque markers are an annular developing support ring; or the radiopaque markers are spaced by a plurality of intervals radially.

The multi-lumen stent graft of the present disclosure has following beneficial technical effects:

The multi-lumen stent graft of the present disclosure includes a main body stent graft as a main body stent, a tubular connection stent graft, and a branch stent. The main body stent graft is provided with a sub lumen, and one to three windows are provided on the tubular connection stent graft. The branches can be embedded in the sub lumen and the window for using in the reconstruction of the branches. For patients with type A dissection or aortic arch aneurysm, the positions of the three branch openings on the aortic arch, the size of the inner diameter of the branches, and the angles between the branch vessels and the aortic arch all have certain differences, and if the differences are relatively large, it can occur stent displacement, mismatch, and even increasing of the difficulty of surgery. By using the multi-lumen stent graft according to the present disclosure, a stent of a corresponding size can be selected according to the number, position and thickness of the aortic branch blood vessels to be reconstructed, so as to avoid mismatch. In the released state, the tubular connection stent graft of the present disclosure is partially released and fitted into the main lumen of the main body stent graft, and is firmly attached to the main lumen, which is not prone to endoleakage. The multi-lumen stent graft according to the present disclosure has benefits of simple operation, high flexibility, and wide application range, and is particularly suitable for intraluminal treatment of Stanford A-type dissection or aortic arch aneurysm.

BRIEF DESCRIPTION OF THE DRAWINGS

The present disclosure is further explained below with reference to accompanied drawings and embodiments.

FIG. 13 and FIG. 14 are structural schematic diagrams of a main body stent graft in accordance with different implementation manners of a third embodiment of the present disclosure.

FIG. 15a is a structural schematic diagram of a main body stent graft in accordance with a fourth embodiment of the present disclosure.

FIG. 15b is a structural schematic diagram of a corresponding relationship between a main body stent graft and a connection stent graft in accordance with the fourth embodiment of the present disclosure.

FIG. 16 is a structural schematic diagram of a connection stent graft in accordance with a fifth embodiment of the present disclosure.

FIG. 17 is a structural schematic diagram of a main body support frame connected with a main body covering in accordance with the fifth embodiment of the present disclosure.

DETAILED DESCRIPTION

In order to have a clearer understanding of the technical features, objects, and effects of the present disclosure, specific embodiments of the present disclosure will now be described in detail with reference to the drawings.

Definition of orientations: in surgery, the term "proximal end" in the present disclosure refers to the end near the heart, and the term "distal end" refers to the end far from the heart. The terms of high and low in the present disclosure are relative to the main body covering. The end surface that exceeds the main body covering is called high, and the end surface that does not exceed the main body covering is called low. This definition is only for convenience of expression, and does not limit the direction of the multi-lumen stent graft itself.

Figure 1:
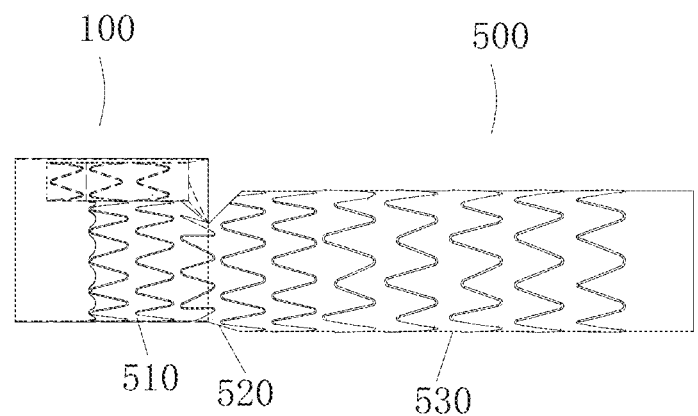
FIG. 1 is a structural schematic diagram of a multi-lumen stent graft after it is assembled in accordance with a first embodiment of the present disclosure.
Figure 2:
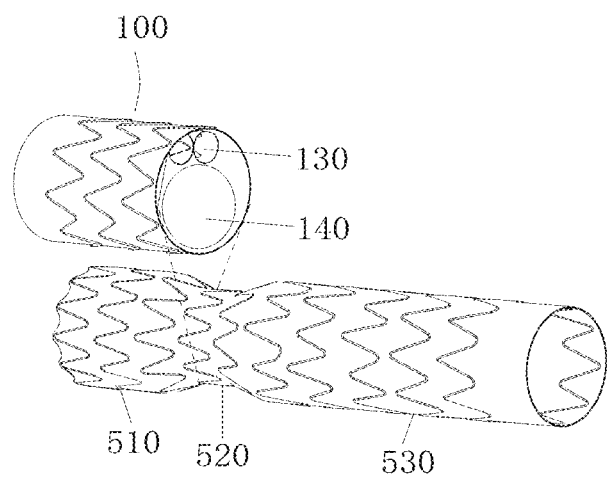
FIG. 2 is a structural schematic diagram of a multi-lumen stent graft before it is assembled in accordance with the first embodiment of the present disclosure.
Figure 3:
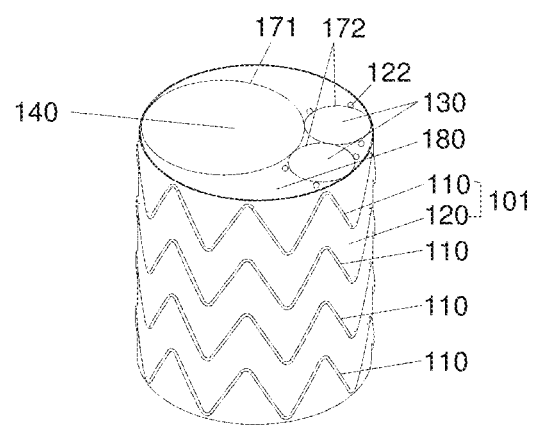
FIG. 3 is a structural schematic diagram of a main body stent graft in accordance with a first implementation manner of the first embodiment of the present disclosure.

First embodiment, as shown in FIGS. 1-3, a multi-lumen stent graft 10 includes a tubular main body stent graft 100 and a tubular connection stent graft 500. The main body stent graft 100 includes a tubular main body stent 101, and the main body stent 101 includes a tubular main body covering 120 and a main body support frame 110 fixed on a wall of the main body covering 120. A main lumen 140 and at least one sub lumen 130 are separated axially by a separation covering within the main body stent 101. In a released state, a proximal end of the connection stent graft and the main lumen 140 at a distal end of the tubular main body stent graft 100 are fitted and connected together.

The multi-lumen stent graft 10 includes two main parts: a tubular main body stent graft 100 and a tubular connection stent graft 500. The two parts are described in detail below:

First, the main body stent graft 100:

As shown in FIG. 3, the main body stent graft 100 includes a tubular main body stent 101. The main body stent 101 includes a tubular main body covering 120, and a main body support frame 110 fixed on a wall of the main body covering 120. A main lumen 140 and at least one sub lumen 130 are separated axially by a separation covering within the main body stent 101. A main lumen opening 171 is provided at a distal end of the main lumen 140 of the main body stent graft 100, and a sub lumen opening 172 is provided at a distal end of the sub lumen 130.

The main body stent 101 is a main structure of the main body stent graft 100, and includes a main body covering 120 and a main body support frame 110. The main body covering 120 is a tubular structure, and a shape of a transverse end face of the main body covering 120 is a circle or an ellipse that cooperates with a blood vessel.

Figure 4:
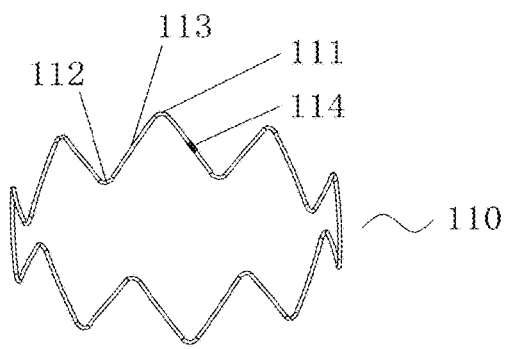
FIG. 4 is a structural schematic diagram of a main body support frame in accordance with the first embodiment of the present disclosure.
Figure 5:
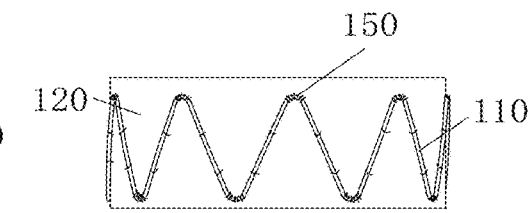
FIG. 5 is a structural schematic diagram of a main body support frame connected with a main body covering in accordance with the first embodiment of the present disclosure.

The main body support frame 110 is stitched on the main body covering 120. The main body support frame 110 has various implementation manners. The first implementation manner of the main body support frame 110: as shown in FIG. 4, the main body support frame 110 is a plurality of axially arranged annular wave-shaped support frames, the annular wave-shaped support frames may be equal-height wave stent, high-low wave stent, etc. The structures used for the stent graft are suitable for the present disclosure. It will not repeat herein. In this embodiment, as shown in FIGS. 4-5, the main body support frame 110 is composed of multiple Z-shaped or sine waves, and each Z-shaped or sine wave has a peak 111 and an adjacent valley 112. A connecting rod 113 is disposed between the peak 111 and the adjacent valley 112. Each circle of the annular main body support frame 110 is made of a super-elastic nickel-titanium wire. The super-elastic nickel-titanium alloy wire has a selectable wire diameter (that is, a diameter) of 0.3 mm to 0.55 mm. In the first embodiment, a nickel-titanium wire with a diameter of 0.5 mm is used for weaving, the number of Z-shaped or sine waves is 9, and the vertical height of the annular support frame is 11 mm. Each circle of the main body support frame 110 has a connecting steel sleeve 114, and the two ends of the nickel-titanium wire are inside the connecting steel sleeve 114, and then the two ends of the nickel-titanium wire are fixed to the inside of the steel sleeve by mechanical compression or welding.

The second implementation manner of the main body support frame 110: it is a woven mesh structure or a cut mesh structure. This structure is also a commonly used structure, and is not repeated here.

The main body covering 120 is made of polyester cloth or other polymer materials. The main body covering 120 is cylindrical in the axial direction as a whole. The main body support frame 110 is sutured to the main body covering 120 by a suture 150. The main body support frame 110 and the covering 120 are connected by the stitching method shown in FIG. 5. The suture 150 along the waveform of the main body support frame 110 accompanies the entire main body support frame 110. The suture 150 sutures the main body support frame 110 over the covering 120 by several non-equally spaced suture nodules. The diameter of the suture 150 on the covering 120 is selected from 0.05 mm to 0.25 mm. The diameter of the suture 150 in this embodiment is 0.1 mm.

The main body covering 120 may also be made of polytetrafluoroethylene or other polymer materials, and the main body support frame 110 may be fixedly connected to the main body covering 120 by hot pressing.

Figure 6:
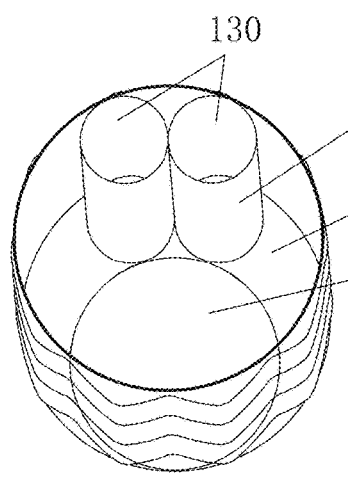
FIG. 6 and FIG. 7 are structural schematic diagrams of a main body stent graft from another direction in accordance with the first embodiment of the present disclosure.

As shown in FIG. 6, the inner lumen at the distal end of the main body stent 101 is divided into a multi-lumen structure, i.e., a main lumen 140 and at least one sub lumen 130 are separated axially by a separation covering 131 within the inner lumen of the main body stent 101. In general, the sub lumen 130 is enclosed by the separation covering 131 independently. The empty lumen between the separation covering 131 and the main body covering 120 is the main lumen 140. This design can reduce the overall diameter of the stent in the gripped state and can reduce the diameter of the delivery system used to assemble the sheath. The diameter of the main lumen 140 is greater than the diameter of the sub lumen 130, and the number of sub lumens 130 can be set according to actual needs, generally between one to three. The shapes of transverse end faces of the main lumen 140 and the sub lumen 130 are circular, oval, fusiform, or irregularly curved. As shown in FIG. 3, in this embodiment, one circular main lumen 140 and two circular sub lumens 130 are provided.

Figure 7:
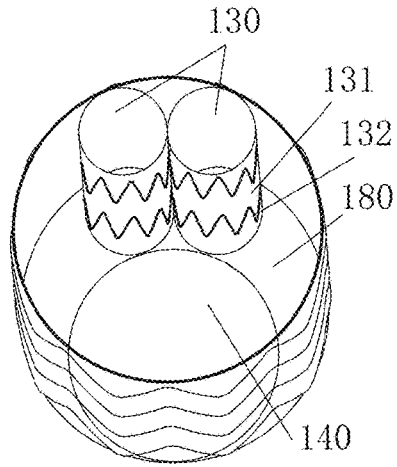

As shown in FIG. 6, the separation covering 131 may be provided independently, or a support frame 132 may be fixed on the wall of the separation covering 131 as shown in FIG. 7. The structure of the support frame 132 may be a braided mesh support frame, or may be a plurality of annular wave-shaped support frames arranged axially.

As shown in FIG. 3 and FIGS. 6-8, a covering for connecting and closing the inner lumen is provided between the separation covering 131 and the main body covering 120. That is, at least a transversal covering 180 is provided between the distal end of the main body covering 120 and the separation covering 131. The transverse covering 180 connects the main body covering 120 and the separation covering 131 together and seals the main lumen 140, that is, sealing the gap between the main body stent 101 and the sub lumen 130. The transverse covering 180 is disposed at least at the distal end of the main body covering 120, and can also be disposed at both the proximal end and the distal end of the main body covering 120. Compared with the main body covering 120 and the separation covering 131, the transverse covering 180 is arranged radially or approximately radially.

The transverse covering 180 is a structure for transversal closure. There are many implementation manners. This embodiment is the first implementation manner: the transverse covering 180 is a planar structure perpendicular to the central axis of the main body stent 101. The transverse covering 180 is located at the distal end of the main body covering 120 and is stitched together with the main body covering 120 by stitching.

The main lumen opening 171 is an opening for connection provided at the distal end of the main lumen 140, and its diameter is smaller than the diameter of the main body covering, and generally larger than the diameter of the lumen body of the sub lumen 130. The sub lumen opening 172 is set at the distal end of the sub lumen 130. The diameter of the sub lumen opening 172 may be smaller than the diameter of the sub lumen 130, and may be the same as the diameter of the sub lumen 130. In this embodiment, the diameter of the sub lumen opening 172 is the same as the diameter of the sub lumen 130. The main lumen opening 171 and the sub lumen opening 172 are formed on the transverse covering 180.

Figure 8:
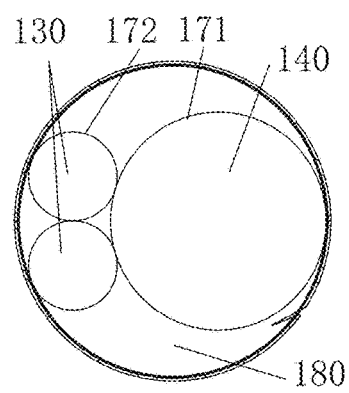
FIG. 8 is a structural schematic diagram of an end face of a main body stent graft in accordance with the first embodiment of the present disclosure.

In this embodiment, the main lumen opening 171 and the sub lumen opening 172 are disposed on the transverse covering 180. The main lumen opening 171, the sub lumen opening 172 have different positional relationships with each other. The first implementation manner is: there is a gap among the axial projections of all three of the main lumen opening 171, the sub lumen opening 172, and the main body stent 101; the second implementation manner is: the axial projections of at least two out of all three of the main lumen opening 171, the sub lumen opening 172, and the main body stent 101 are abutted against each other without a gap; the third implementation manner is: the main lumen opening 171 is simultaneously formed by a side wall of the main body stent 101 and the separation covering 131. The positional relationship between the main lumen opening 171 and the sub lumen opening 172 in the radial direction is shown in FIG. 8. The main lumen opening 171 is disposed near the main body covering 120, and the sub lumen openings 172 are disposed together on the side of the main lumen opening 171. The number of the sub lumen opening 172 is set as two. In order to reduce the radial size as a whole and maintain the dimensions of the main lumen opening 171 and the sub lumen opening 172, the main lumen opening 171 and the sub lumen opening 172 are arranged tangentially.

In the axial direction, the main lumen opening 171 and the sub lumen opening 172 have different implementation manners, and this embodiment is the first implementation manner: the end faces of the main lumen opening 171, the sub lumen opening 172, and the main body covering 120 are at least even at the distal end; in this embodiment, the main lumen opening 171 and the sub lumen opening 172 are provided on the transverse covering 180.

The main lumen opening 171 can define the opening by a suture, or an annular support frame can be provided. The structure of the annular support frame can be adapted to the shape of the opening, such as circular, to prevent the main lumen opening 171 from deforming after being compressed. The proximal end of the sub lumen 130 and the distal end of the sub lumen opening 172 can also be sutured, or an annular frame may be adopted, or a ring and an annular frame can be used to support the sub lumen opening 172. The separation covering 131 on the circumference of the sub lumen 130 extends from the distal end, that is, the sub lumen opening 172 extends to the proximal end, to form a tubular structure. As shown in FIG. 7, a support frame 132 may be fixed on the outer surface or the inner surface of the separation covering 131, and the support frame 132 is an annular support covering frame or a woven mesh frame.

In order to facilitate the operation, the main lumen opening 171 and the sub lumen opening 172 are respectively provided with radiopaque markers 122 for displaying positions of the openings of the main body stent graft 100 during surgery. Developing point 122 selects developing materials. It is particularly preferred that the developing point 122 is an annular developing support ring; the support ring is preferably a super-elastic material with developing performance. Alternatively, as shown in FIG. 3, the radiopaque markers 122 are spaced a plurality of times in a radial direction.

Figure 9:
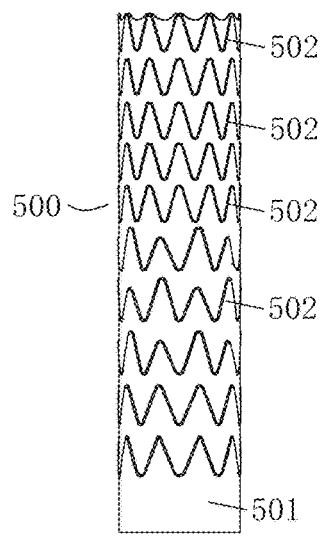
FIG. 9 to FIG. 10c are structural schematic diagrams of a connection stent graft in accordance with different implementation manners of the first embodiment of the present disclosure.
Figure 10A:
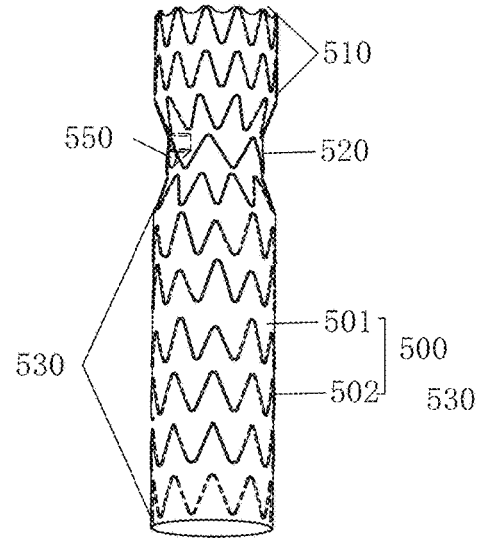
Figure 10B:
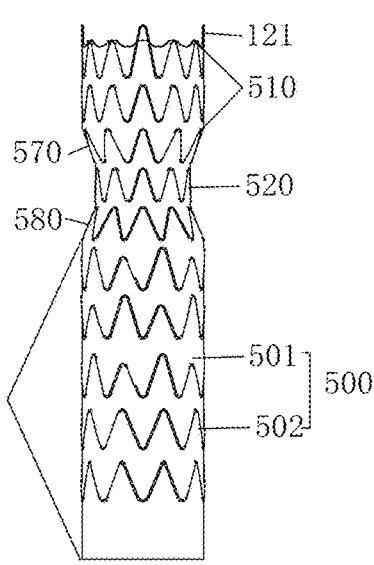
Figure 10C:
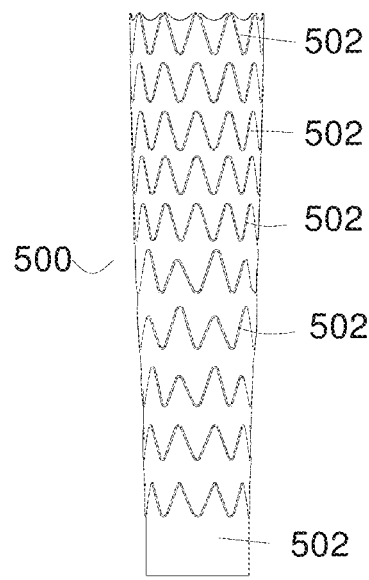

Second, the Connection Stent Graft:

The connection stent graft 500 includes a connection covering 501 and a connection support frame 502 fixed on the connection covering 501. The structure of the connection stent graft 500 can be an isodiametric stent as shown in FIG. 9 or a non-isodiametric stent as shown in FIGS. 10a-10b. The isodiametric stent refers to the diameter of the connection stent graft 500 is the same at different positions in the axial direction. Non-isodiametric stent refers to the diameter of the connection stent graft 500 is different at different positions in the axial direction. As shown in FIGS. 10a-10b, the connection stent graft 500 is a non-isodiametric stent composed of, from a proximal end to a distal end sequentially, a first tubular body 510, a second tubular body 520, and a third tubular body 530. The diameter of the second tubular body 520 is smaller than the diameter of the first tubular body 510 and the diameter of the third tubular body 530. Transition portions 521 and 522 can also be disposed between the first tubular body 510, the second tubular body 520, and the third tubular body 530. As shown in FIG. 10c, the connection stent graft 500 is a non-isodiametric stent. The diameter of the proximal end of the non-isodiametric stent is greater than the diameter of the distal end, and the diameter gradually decreases from the proximal end to the distal end. The entire stent forms a uniform round table structure, so as to adapt to the morphology of the blood vessel whose diameter changes from the proximal end to the distal end.

The connection covering 501 is made of polyester cloth or other polymer materials. The connection covering 501 of the isodiametric stent is cylindrical, and the connection covering 501 of the non-isodiametric stent is a tubular structure with different axial diameters.

The connection support frame 502 is a high-low wave stent or an equal-height wave stent. As shown in FIG. 10b, the high-low wave stent is a partially-sutured stent. The connection support frame 502 is sutured to the connection covering 501 by a suture. The specific stitching method is the same as that of the main body covering 120 and the main body support frame 110.

As shown in FIG. 1, the tubular main body stent graft 100 is combined with the connection stent graft 500. When used, the proximal end of the connection stent graft 500 is released in the tubular main body stent graft 100, i.e., in the main lumen 140 of the main body stent graft 100. The diameter of the main lumen opening 171 is smaller than the diameter of a part of the proximal end of the connection stent graft 500 after releasing. The main lumen 140 compresses a part of the proximal end of the connection stent graft 500, so that the tubular body of the connection stent graft 500 fits the wall of the main lumen 140 to prevent endoleaks.

Figure 11:
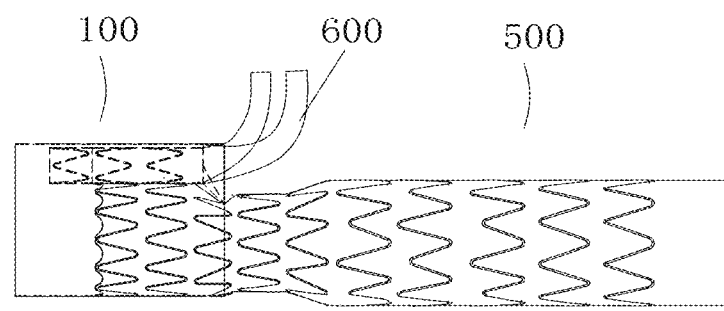
FIG. 11 is a structural schematic diagram of a multi-lumen stent graft assembled with a branch stent in accordance with the first embodiment of the present disclosure.

When released, the delivery device is pushed along the super-hard guide wire, to push the pre-installed main body stent graft 100 to the position of the thoracic aortic dissection, and locate it through the development ring at the front end of the outer sheath and the developing point 122 at the distal end of the main body stent graft 100; by operation of the fixed handle and slide handle of the delivery device, the main body stent graft 100 is released. Then the tubular connection stent graft 500 is released according to the same steps, so that the proximal end of the connection stent graft 500 is fitted into the main lumen 140 of the main body stent graft 100. After expansion, the proximal end of the connection stent graft 500 is locked by the main lumen 140 and the main lumen opening 171 to form a tight fitting to prevent the connection stent graft 500 from being disengaged from the main body stent graft 100, and finally the small branch stent 600 is released. After releasing is illustrated in FIG. 11.

Figure 12:
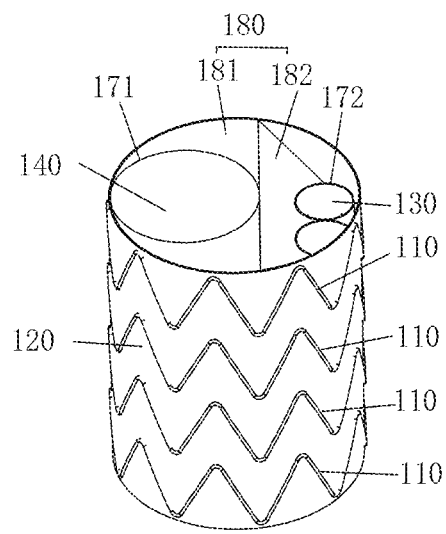
FIG. 12 is a structural schematic diagram of a main body stent graft in accordance with a second embodiment of the present disclosure.

The second embodiment, as shown in FIG. 12, this embodiment is an improvement based on the first embodiment. That is, the difference is that the second implementation manner of the transverse covering 180: the transverse covering 180 includes at least one planar structure 181 and at least one inclined surface structure 182, that is, the transverse covering 180 is a combination of the planar structure 181 and the inclined surface structure 182. The way of combination is that the planar structure 181 and the inclined surface structure 182 are the whole of an integrated structure or they are connected together to form a whole. Due to the existence of the inclined surface structure 182, at least one of the main lumen opening 171 and the sub lumen opening 172 is higher or lower than the end face of the main body covering 120.

Regarding the inclined surface structure 182, when the end face of the main lumen 140 is higher than the end face of the sub lumen 130, the inclined surface structure 182 is inclined in a direction from the main lumen 140 to the sub lumen 130. That is, the main lumen opening 171 is higher than the sub lumen opening 172. According to the position where the inclination starts, the inclined surface structure 182 may be inclined from the outer edge of the main lumen opening 171 or the tangent of the outer wall surface of the extension covering or in a direction from outside the tangent to the sub lumen 130; the inclined surface structure may also be inclined in a direction from the intersection between the main lumen opening 171 and the main body covering 120 to the sub lumen 130. As shown in FIG. 12, this embodiment is inclined in a direction from the tangent of the outer edge of the main lumen opening 171 to the sub lumen 130. The recessed axial length of the sub lumen opening 172 relative to the main lumen opening 171 is 5 mm. By simultaneously connecting the sub lumen 130, the main lumen 140, and the main body covering 120 while suturing inwardly relative to the end face of the distal end of the main body stent 101, it can further enhance the stability of the joint after the introduction of the branch stent. The covering at the distal end of the main body covering 120 corresponding to the position of the sub lumen opening 172 can be cut into two V-shapes or U-shapes. When the main body stent 101 is used with a small braided stent or a cuff stent or other branch stent, it can increase the visibility of the circumferential sub lumen 130, and facilitates the accurate releasing of branch stents.

The above structures can be adapted to the distal end of the main body stent 101 and also to the proximal end of the main body stent 101.

The rest of the structure is the same as the first embodiment and will not be repeated herein.

Figure 13:
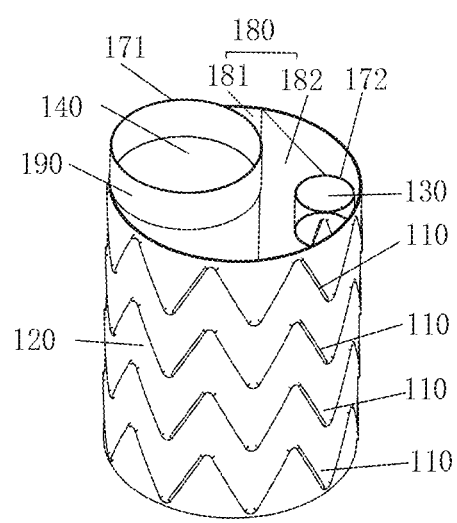

The third embodiment, as shown in FIGS. 13-14, this embodiment is an improvement based on the second embodiment. That is, at least one of the main lumen 140 and the sub lumen 130 has a cylindrical extension covering 190 extending in a direction from the transverse covering 180 to the distal end. The axial length of the extension covering 190 is 5 to 10 mm.

The extension covering 190 may be formed by the separation covering 131 directly extending toward the distal end, or may be formed by extending the opening provided on the transverse covering 180 corresponding to the main lumen 140 toward the distal end. The end face of the extension covering 190 forms the main lumen opening 171, and the main lumen opening 171 is higher than, lower than, or even with the end face of the main body covering 120; the end face of the extension covering forms the sub lumen opening 172, and the sub lumen opening 172 is higher than, lower than, or even with the end face of the main body covering 120. The other is the opening at the distal end of the extension covering 190 is the main lumen opening 171. The sub lumen opening 172 is the opening at the distal end of the extension covering. As shown in FIG. 13, the main lumen 140 and the sub lumen 130 are respectively provided with an extension covering 190.

The extension covering 190 may be set separately, or as shown in FIG. 14, an inner wall or an outer wall of the extension covering 190 is provided with an extension support frame 191 for supporting the extension covering 190. The extension support frame 191 is a waveform support frame or a braided support frame.

When the multi-lumen stent graft is used in combination with a branch stent, the extension covering 190 can further improve the connection stability of the main lumen 140 and the branch stent.

The rest of the structure is the same as the second embodiment, and will not be repeated here.

The fourth embodiment, as shown in FIGS. 15*a*-15*b*, this embodiment is an improvement based on the second embodiment or the third embodiment. The improvement is that the transverse covering 180 is a third implementation manner: the transverse covering 180 is an inclined surface structure that is not perpendicular to the central axis of the main body stent 101; the inclined surface structure is inclined in a direction from the intersection between the main lumen opening 171 and the main body covering 120 to the sub lumen 130. The main lumen opening is composed of the side wall of main body stent 101 and the separation covering 131 at the same time. That is, the main lumen opening 171 is a structure formed by the separation covering 131 and the main body covering 120. The structure is fusiform, or oblate, or semicircular.

The proximal end and the distal end of the main body covering 120 may further be provided with a bare stent 121. The structure of the bare stent 121 is a wave-shaped support frame, which is fixed on the main body covering 120 by stitching.

FIG. 15*b* shows the corresponding relationship between the main body stent graft 100 and the connection stent graft 500. The proximal end of the connection stent graft 500 corresponds to the main lumen 140 of the main body stent graft 100. The fitting position is the position of the second tubular body 520 of the connection stent graft 500.

The rest of the structure is the same as the second embodiment or the third embodiment, and will not be repeated herein.

The fifth embodiment, as shown in FIGS. 16-17, this embodiment is an improvement based on the first, second, third, and fourth embodiments. The improvement is that the connection stent graft 500 has a window 550 in which a small branch is embedded. Specifically, a window 550 is opened on the connection covering 501.

As shown in FIG. 16, for the isodiametric stent, the side wall of the isodiametric stent is provided with a window 550 in which a small branch is embedded; when the main body stent graft 100 and the connection stent graft 500 are fitted, the window 550 in which the small branch is embedded is near sub lumen 130 of the main body stent graft 100, referring to FIG. 17. The position of the window 550 is located at a position away from the proximal end ⅓-⅔ of the tubular connection stent graft 500. When the tubular connection stent graft 500 is assembled to the aortic arch, the window 550 can establish a channel with the innominate artery.

Figure 18:
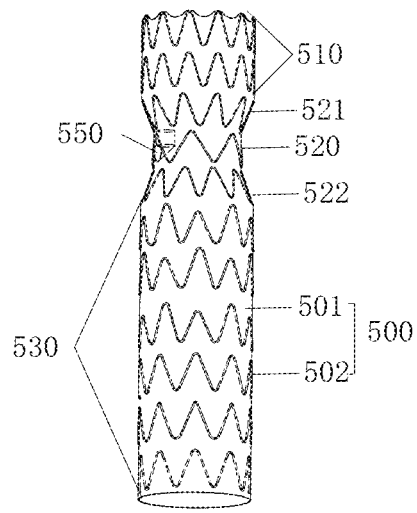
FIG. 18 is a structural schematic diagram of a connection stent graft in accordance with the fifth embodiment of the present disclosure.
Figure 19:
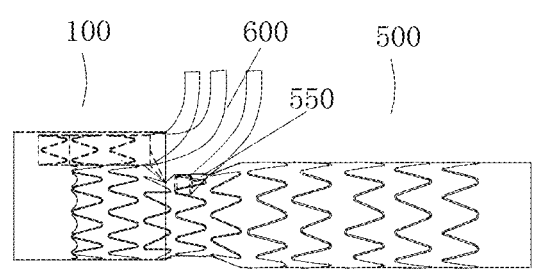
FIG. 19 is a structural schematic diagram of a multi-lumen stent graft assembled with a branch stent in accordance with the fifth embodiment of the present disclosure.

As shown in FIGS. 18-19, for a non-isodiametric stent, the second tubular body 520 has a window 550 in which a small branch is embedded. When the main body stent graft 100 and the connection stent graft 500 are fitted, the window 550 in which the small branch is embedded is close to the sub lumen 130 of the main body stent graft 100. The transition portion disposed between the second tubular body 520 and the third tubular body 530 may be provided with a window 550 in which a small branch is embedded.

As shown in FIG. 19, in this embodiment, the connection stent graft 500 is combined with the main body stent 101 in the main body stent graft 100, and the two sub lumens 130 in the main body stent graft 100 are respectively connected to the small braided stent 600 or other cuff stents, to establishes a channel of the left subclavian artery and the left common carotid artery. A window 550 of the tubular connection stent graft 500 is connected to the innominate artery to establish an innominate artery channel.

As shown in FIG. 19, when the proximal end of the connection stent graft 500 is released in the main lumen 140 of the main body stent 101, the position of the window 550 should be on the same side as the sub lumen 130 of the main body stent 101, so that the a small branch embedded inside the window 550 can connect small braided stents to establish innominate arterial channels.

Figure 20:
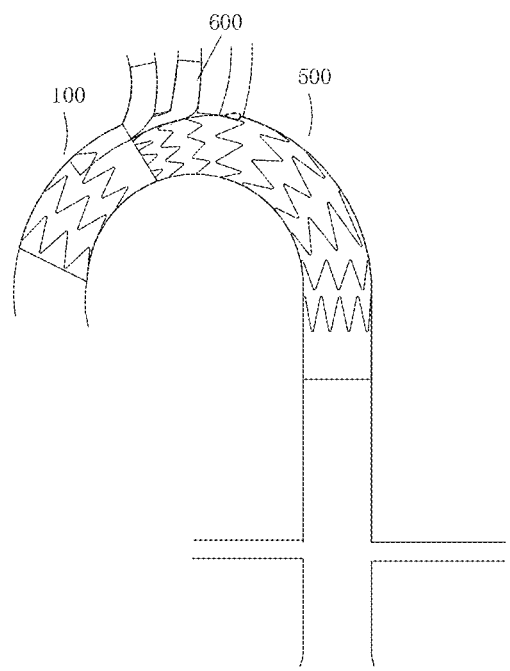
FIG. 20 is a schematic diagram of a multi-lumen stent graft after releasing in the thoracic aorta in accordance with the fifth embodiment of the present disclosure.

In another implementation manner, as shown in FIG. 20, a tubular connection stent graft 500 with windows and embedded branches can also be selected and used in combination with a suitable main body stent graft 100. In use, the tubular connection stent graft 500 can be released in the main lumen 140 of the main body stent graft 100, and a cooperative position of the branch tubular connection stent graft 500 and the distal end of the main lumen 140 of the main body stent graft 100 is at the first tubular body 510 or in a transition portion between the first tubular body 510 and the second tubular body 520. The diameter of the main lumen 140 is smaller than the diameter of the first tubular body 510 of the branch tubular connection stent graft 500. The main lumen 140 compresses the first tubular body 510, and the first tubular body 510 fits the wall of the main lumen 140 to prevent endoleaks.

When released, the convey is pushed along the super-hard guide wire to push the pre-installed main body stent graft 100 to the position of the thoracic aortic dissection, and location is performed by the development ring at the front end of the outer sheath and the developing point 122 at the distal end of the main body stent graft 100. By operation of the fixed handle and slide handle of the convey, the main body stent graft 100 is released. Then the tubular connection stent graft 500 is released according to the same steps, so that the proximal end of the connection stent graft 500 is fitted into the main lumen 140 of the main body stent graft 100. After expansion, the proximal end of the connection stent graft 500 is locked by the main lumen 140 and the main lumen opening 171 to form a tight fitting to prevent the connection stent graft 500 from being disengaged from the main body stent graft 100, and finally the small braided stent is released. It is shown in FIG. 20 after release.

The diameter of the second tubular body 520 of the connection stent graft 500 is smaller than the diameter of the first tubular body 510. When the two sub lumens 130 of the main body stent graft 100 are assembled with a small woven branch bracket, the position of the second tubular body 520 of the connection stent graft 500 can provide sufficient space to avoid stent stacking.

In this embodiment, two sub lumens 130 of the main body stent graft 100 are respectively connected to a small braided stent or other cuff stent, to establish a channel of the left subclavian artery and the left common carotid artery, and a branch tubular connection stent graft 500 is connected to the small braided stent to establish an innominate arterial channel.

According to the specific location of the three branch openings on the patient's aortic arch, the internal diameter of the branch, and the angle between the branch vessel and the aortic arch, an appropriate combination of the main body stent graft 100 and the connection stent graft can be selected.

The rest of the structure is the same as those of the first, second, third, and fourth embodiments, and details are not described herein again.

Figure 21:
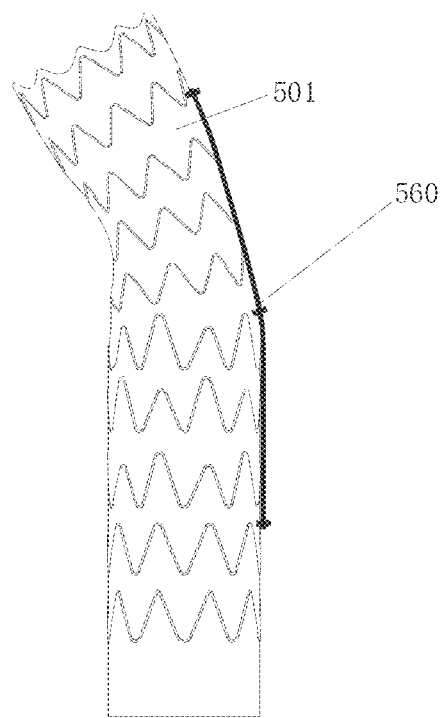
FIG. 21 is a structural schematic diagram of a connection stent graft in accordance with a sixth embodiment of the present disclosure.

The sixth embodiment, as shown in FIG. 21, this embodiment is an improvement based on the first, second, third, fourth, and fifth embodiments. The improvement is that a support rod 560 is fixed to the outer wall of the connection covering 501 in the axial direction. The support rod 560 is disposed on the connection covering 501 on the side near the sub lumen 130.

There is at least one fixing point 561 between the support rod 560 and the connection covering 501 for fixing the two together.

The rest of the structure is the same as the first, second, third, fourth, and fifth embodiments, and details are not described herein again.

The above disclosure are only embodiments of the present disclosure, but the present disclosure is not limited to these embodiments, and those skilled in the art can make various changes and modifications to the present disclosure without departing from the spirit and scope of the present disclosure. Obviously, these changes and modifications should fall into the protection scope required by the present disclosure. In addition, although some specific terms are used in this specification, these terms are just for convenience of explanation and do not constitute any special restriction on the present disclosure.

What is claimed is:

1. A multi-lumen stent graft, comprising a tubular main body stent graft and a tubular connection stent graft, wherein
    the main body stent graft comprises a tubular main body stent; the main body stent comprises a tubular main body covering and a main body support frame fixed on a wall of the main body covering; and a main lumen and at least one sub lumen are separated axially by a separation covering within the main body stent;
    in a released state, a proximal end of the connection stent graft and the main lumen at a distal end of the tubular main body stent graft are fitted and connected together;
    wherein a transverse covering is provided at least between the distal end of the main body covering and the separation covering, and the main body covering and the separation covering are connected together by the transverse covering, wherein
    the transverse covering comprises at least one planar structure and at least one inclined surface structure, and the planar structure and the inclined surface structure are integral or are connected together.

2. The multi-lumen stent graft according to claim 1, wherein a distal end of the main lumen is provided with a main lumen opening, and an outer diameter of the proximal end of the connection stent graft is larger than the main lumen opening of the main body stent graft; in the released state, the proximal end of the connection stent graft is fitted and connected with the main lumen by the main lumen opening.

3. The multi-lumen stent graft according to claim 1, wherein the connection stent graft is an isodiametric stent, and a side wall of the isodiametric stent is provided with a window in which a small branch is embedded; when the main body stent graft and the connection stent graft are fitted, the position of the window in which the small branch is embedded is on the same side as the sub lumen of the main body stent graft.

4. The multi-lumen stent graft according to claim 1, wherein the connection stent graft is a non-isodiametric stent composed of, from a proximal end to a distal end sequentially, a first tubular body, a second tubular body, and a third tubular body; a diameter of the second tubular body is smaller than a diameter of the first tubular body and a diameter of the third tubular body.

5. The multi-lumen stent graft according to claim 4, wherein a window in which a small branch is embedded is provided on the second tubular body of the connection stent graft or a transition portion disposed between the second tubular body and the third tubular body; when the main body stent graft and the connection stent graft are fitted, the position of the window in which the small branch is embedded is on the same side as the sub lumen of the main body stent graft.

6. The multi-lumen stent graft according to claim 1, wherein the connection stent graft is a non-isodiametric stent whose diameter of the proximal end is larger than the diameter of the distal end, and the diameter of the non-isodiametric stent is tapered from the proximal end to the distal end.

7. The multi-lumen stent graft according to claim 1, wherein the connection stent graft comprises a connection covering and a connection support frame fixed on the connection covering.

8. The multi-lumen stent graft according to claim 7, wherein the connection support frame is selected from the group consisting of high-low wave stents and equal-height wave stents, and the high-low wave stent is a partially-sutured stent.

9. The tubular main body stent graft according to claim 7, wherein a support rod is fixed axially along an outer wall of the connection covering.

10. The multi-lumen stent graft according to claim 9, wherein the support rod is disposed on the connection covering on a side facing the sub lumen.

11. The multi-lumen stent graft according to claim 9, wherein at least one fixing point is disposed between the support rod and the connection covering for fixing both together.

12. The multi-lumen stent graft according to claim 1, wherein
    a main lumen opening is provided at a distal end of the main lumen and a sub lumen opening is provided at a distal end of the sub lumen, and
    in an axial direction, the end faces of the main lumen opening, the sub lumen opening, and the main body covering are even at least at the distal end of the main body covering; or the end face of at least one of the main lumen opening and the sub lumen opening is higher or lower than the end face of the main body covering.

13. The multi-lumen stent graft according to claim 1, wherein at least one of the main lumen and the sub lumen comprises a cylindrical extension covering extending from the transverse covering to the distal end of the main body covering;
    an end face of the extension covering end face forms a main lumen opening, and the main lumen opening is higher, lower, or flush with the end face of the main body covering;
    or the end face of the extension covering forms a sub lumen opening, and the sub lumen opening is higher than, lower than, or flush with the end face of the main body covering.

14. The multi-lumen stent graft according to claim 13, wherein an inner wall or an outer wall of the extension covering is provided with an extension support frame for supporting the extension covering.

15. The multi-lumen stent graft according to claim 1, wherein
a main lumen opening is provided at a distal end of the main lumen and a sub lumen opening is provided at a distal end of the sub lumen, and
the main lumen opening and the sub lumen opening are respectively provided with radiopaque markers for displaying positions of each opening of the shunt during surgery.

16. The multi-lumen stent graft according to claim 15, wherein the radiopaque markers are an annular developing support ring; or the radiopaque markers are spaced by a plurality of intervals radially.

17. The multi-lumen stent graft according to claim 1, further comprising an annular support frame, wherein a main lumen opening is provided at a distal end of the main lumen, and a structure of the annular support frame is adapted to a shape of the main lumen opening to prevent the main lumen opening from deforming after being compressed.

18. The multi-lumen stent graft according to claim 1, further comprising an annular frame, wherein a sub lumen opening is provided at a distal end of the sub lumen, and the annular frame is used for supporting the sub lumen opening.

19. The multi-lumen stent graft according to claim 1, wherein the connection stent graft is provided with a window in which a small branch is embedded, wherein a distance between the window and the proximal end of the connection stent graft is $\frac{1}{3}$ to $\frac{2}{3}$ of an axial length of the connection stent graft.

20. The multi-lumen stent graft according to claim 1, wherein at least one of the main lumen and the sub lumen comprises a cylindrical extension covering extending from the transverse covering to the distal end of the main body covering, wherein an axial length of the extension covering ranges from 5 to 10 mm.

* * * * *